(12) United States Patent
Vola et al.

(10) Patent No.: US 11,020,230 B2
(45) Date of Patent: Jun. 1, 2021

(54) DEVICE FOR PERFORMING OR PREPARING FOR A MITRAL VALVE ANNULOPLASTY BY A TRANSFEMORAL APPROACH

(71) Applicants: CMI'NOV, Monistrol-sur-Loire (FR); Marco Vola, Saint-Priest-en Jarez (FR)

(72) Inventors: Marco Vola, Saint-Priest-en Jarez (FR); Bernard Pain, Monistrol-sur-Loire (FR)

(73) Assignees: CMI'NOV, Monistrol-sur-Loire (FR); Marco Vola, Saint-Priest-en Jarez (FR)

( * ) Notice: Subject to any disclaimer, the term of this patent is extended or adjusted under 35 U.S.C. 154(b) by 215 days.

(21) Appl. No.: 16/469,201

(22) PCT Filed: Dec. 7, 2017

(86) PCT No.: PCT/FR2017/053444
§ 371 (c)(1),
(2) Date: Jun. 13, 2019

(87) PCT Pub. No.: WO2018/109329
PCT Pub. Date: Jun. 21, 2018

(65) Prior Publication Data
US 2020/0100898 A1    Apr. 2, 2020

(30) Foreign Application Priority Data
Dec. 15, 2016 (FR) .................................. 1662559

(51) Int. Cl.
*A61F 2/24* (2006.01)
(52) U.S. Cl.
CPC .......... *A61F 2/2466* (2013.01); *A61F 2/2445* (2013.01); *A61F 2220/0008* (2013.01);
(Continued)

(58) Field of Classification Search
CPC ......... A61F 2/24; A61F 2/2466; A61F 2/2445
(Continued)

(56) References Cited

U.S. PATENT DOCUMENTS

| 8,430,926 B2* | 4/2013 | Kirson ................. A61F 2/2418 |
| | | 623/2.37 |
| RE46,126 E * | 8/2016 | Kirson ................. A61F 2/2412 |

(Continued)

FOREIGN PATENT DOCUMENTS

| WO | WO 2007/136783 | 11/2007 |
| WO | WO 2014/195786 | 12/2014 |
| WO | WO 2018/109329 | 6/2018 |

OTHER PUBLICATIONS

Rapport de Recherche Internationale et l'Opinion Ecrite [International Search Report and the Written Opinion] dated Feb. 28, 2018 From the International Searching Authority Re. Application No. PCT/FR2017/053444 and Its Translation of Search Report Into English. (14 Pages).

*Primary Examiner* — Suzette J Gherbi

(57) ABSTRACT

The device (1) is intended to be positioned in a sealed introducer placed in a femoral vein in order to penetrate the left atrium (4) of the heart (3) by passing through the septal wall (5) thereof. The device comprises an assembly for cooperating with a handle under the control of control means for actuation of the assembly, for placing and fixing a reinforcement ring (7) on the mitral valve (2), said assembly being arranged at the end of a manipulation rod (6) and comprising: a bearing member (8) comprising a plurality of arms (8a) connected pivotably to the end of the rod (6) so as to change, under the action of the control means, from a position folded along the rod (6) to a deployed position spaced apart from the rod (6), in order to bear under the mitral valve (2) in a manner uniformly distributed along the periphery of the mitral valve; a counter-bearing member (Continued)

(12) comprising a plurality of arms (12a), at the free end of which arms (12a) the reinforcement ring (7) is arranged, the arms (12a) are connected pivotably to a support (13) disposed coaxially with respect to the rod (6) in such a way as to change, under the action of the control means, from a position folded along the rod (6) to a deployed position spaced apart from the rod (6), in order to realize the counter-bearing on the mitral valve and to position the reinforcement ring (7); means for removing sutures for fixing the reinforcement ring (7) to the mitral valve.

10 Claims, 16 Drawing Sheets

(52) U.S. Cl.
CPC ............... *A61F 2220/0016* (2013.01); *A61F 2250/0065* (2013.01); *A61F 2250/0096* (2013.01); *A61F 2250/0098* (2013.01)

(58) Field of Classification Search
USPC .................................................. 623/2.1–2.19
See application file for complete search history.

(56) References Cited

U.S. PATENT DOCUMENTS

| | | | |
|---|---|---|---|
| 9,517,130 B1* | 12/2016 | Alon | A61B 17/0401 |
| 2007/0168024 A1* | 7/2007 | Khairkhahan | A61F 2/2418 |
| | | | 623/2.18 |
| 2008/0027483 A1* | 1/2008 | Cartledge | A61F 2/2448 |
| | | | 606/201 |
| 2008/0300677 A1* | 12/2008 | Schrayer | A61M 29/02 |
| | | | 623/2.12 |
| 2010/0042208 A1* | 2/2010 | Herrmann | A61F 2/243 |
| | | | 623/2.11 |
| 2010/0198211 A1* | 8/2010 | Kassab | A61B 17/320758 |
| | | | 606/32 |
| 2011/0029072 A1* | 2/2011 | Gabbay | A61F 2/2418 |
| | | | 623/2.23 |
| 2011/0196480 A1* | 8/2011 | Cartledge | A61B 17/12 |
| | | | 623/2.11 |
| 2011/0202130 A1* | 8/2011 | Cartledge | A61F 2/2448 |
| | | | 623/2.37 |
| 2011/0208295 A1* | 8/2011 | Cartledge | A61B 17/0644 |
| | | | 623/2.11 |
| 2011/0257728 A1 | 10/2011 | Kuehn | |
| 2013/0090728 A1* | 4/2013 | Solem | A61F 2/2403 |
| | | | 623/2.12 |
| 2013/0331930 A1 | 12/2013 | Rowe et al. | |
| 2014/0188125 A1* | 7/2014 | Kassab | A61B 17/320758 |
| | | | 606/114 |
| 2014/0296969 A1* | 10/2014 | Tegels | A61F 2/2412 |
| | | | 623/2.11 |
| 2014/0303722 A1* | 10/2014 | Alkhatib | A61F 2/24 |
| | | | 623/2.11 |
| 2015/0209144 A1* | 7/2015 | Khairkhahan | A61F 2/2427 |
| | | | 623/2.11 |
| 2016/0045312 A1* | 2/2016 | Braido | A61F 2/24 |
| | | | 623/2.37 |
| 2016/0074160 A1* | 3/2016 | Christianson | A61F 2/2418 |
| | | | 623/2.18 |
| 2017/0071654 A1* | 3/2017 | Kassab | A61B 17/221 |
| 2019/0117397 A1* | 4/2019 | Alon | A61F 2/2466 |
| 2019/0175341 A1* | 6/2019 | Cartledge | A61F 2/2418 |
| 2019/0290433 A1* | 9/2019 | Mohl | A61F 2/2445 |
| 2020/0155316 A1* | 5/2020 | Alon | A61B 17/0401 |
| 2020/0163769 A1* | 5/2020 | Alon | A61B 17/0401 |
| 2020/0188092 A1* | 6/2020 | Metcalf | A61F 2/243 |

* cited by examiner

DEVICE FOR PERFORMING OR PREPARING FOR A MITRAL VALVE ANNULOPLASTY BY A TRANSFEMORAL APPROACH

RELATED APPLICATIONS

This application is a National Phase of PCT Patent Application No. PCT/FR2017/053444 having International filing date of Dec. 7, 2017, which claims the benefit of French Patent Application No. 1662559 filed on Dec. 15, 2016. The contents of the above applications are all incorporated by reference as if fully set forth herein in their entirety.

FIELD AND BACKGROUND OF THE INVENTION

The invention concerns a device for performing or preparing an annuloplasty of the heart's mitral valve by a transfemoral approach.

In other words, the goal of the annuloplasty is to reduce the caliber of the mitral annulus by shortening, through plication of the small valve attachment, the support point between the commissures. A commissure is understood to be narrowing the perimeter of the posterior part of the mitral annulus by creating points of plication on it, resulting in a reduction in the antero-posterior and side-to-side diameter of the mitral valve.

The invention also finds an advantageous application for the placement of a preventive ring, known as a preparation or attachment ring, on the mitral annulus, intended to subsequently receive a mitral valve implant.

DESCRIPTION OF THE PRIOR ART

Mitral annuloplasty is performed as a way to correct a mitral leak, and works by dilating the mitral annulus (with loss of coaptation of the valve margins) or as an addition to correction of the leak with another mechanism (mitral valve prolapse) to increase the coaptation of the posterior mitral valve in relation to the anterior mitral valve Mitral annuloplasty is a long and difficult procedure that requires the opening of one of the heart chambers and the chest cavity with extracorporeal blood circulation.

A known solution in the state of the art is to use the transapical pathway, i.e., to pass directly to the apex of the heart. One such solution is found, for example, in the explanation in document WO 2014/147336.

This document describes a device to be positioned in a sealed introducer placed in the chest cavity between two ribs to enter the left ventricle through the apex of the heart. The device comprises a body fitted with a handle and at least one control element capable of acting on an assembly to place and fix a strap to the mitral annulus by means of suture elements. This device is advantageous in that the assembly has the means to allow the suture to be extracted through the mitral annulus by being able to tighten the strap and anchor itself on the periphery of the mitral annulus through the pinching effect of said suture by exerting two opposing pressure-bearing forces.

Attachment of the implant to the mitral annulus is improved by exerting a bearing force and an opposing counter-bearing force for precise perforation and passage of anchoring material in a relatively short time and without weakening the adjacent tissue.

However, this type of device can be further improved. The device of the prior art is designed to pass through the chest cavity between two ribs to enter the left ventricle through the apex of the heart, and thus requires a difficult and invasive surgical procedure.

SUMMARY OF THE INVENTION

The goal of the invention is to remedy these disadvantages of the prior art simply, safely, effectively, and rationally.

The problem that the invention proposes to solve is to facilitate the mitral annuloplasty operation.

To achieve this, a device has been developed to perform or prepare a transfemoral annuloplasty of the mitral valve, intended to be positioned in a sealed introducer placed in a femoral vein to penetrate the left atrium of the heart through the septal wall.

The device of the invention comprises an assembly for cooperating with a handle under the control of control means to actuate the assembly, and for placing and attaching a reinforcement ring, possibly made of fabric for example, on the mitral annulus. The assembly is arranged at the end of a manipulation rod and includes:
  a bearing member comprising a plurality of arms connected pivotably to the end of the rod so as to change, under the action of the control means, from a position folded along the rod to a deployed position spaced from the rod in order to provide support under the mitral annulus in a manner uniformly distributed along the periphery of the mitral valve;
  a counter-bearing member comprising a plurality of arms, at the free end of which arms the reinforcement ring is arranged, with the arms connected pivotably to a support disposed coaxially with respect to the rod in such a way as to change, under the action of the control means, from a position folded along the rod to a position spaced away from the rod to create the counter-support on the mitral annulus and position the reinforcement ring;
  means for extracting the sutures for attaching the reinforcement ring to the mitral annulus.

In this way and advantageously, by combining a handle and operating means that are not part of the invention, the device of the invention makes it possible for the mitral annuloplasty procedure to be performed using the transfemoral route to come up through the vena cava. This procedure is less complicated and minimally invasive. The active device assembly navigates through the vena cava where blood pressure is relatively low. The device also makes it possible to prepare for a subsequent annuloplasty procedure by enabling the placement of a reinforcement ring in the form of a preventive ring, known as a preparation or attachment ring, intended to receive a mitral valve implant at a later time.

According to other advantageous features of the invention, considered alone or in combination:
  the arms of the bearing and/or counter-bearing member move simultaneously or selectively from the folded position to the deployed position;
  the arms of the bearing and/or counter-bearing member are arranged inside a sheath in the folded position, and are pushed out of the sheath and are self-expanding in the deployed position;
  the arms of the bearing member and/or the counter-bearing member each include a radiopaque and/or ultrasound marker;

the arms of the bearing and/or counter-bearing member are telescoping;

the means to allow the extraction of clips comprise a plurality of arms connected pivotably to a support disposed coaxially to the rod so as to change, under the action of the control means, from a folded position along the rod to a deployed position spaced away from the rod that aligns with the arms of the counter-bearing member, each arm internally comprising an extractable clip to anchor on the periphery of the mitral valve and attach the reinforcement ring thereto;

each arm of the bearing member is curved, articulated, or flexible to facilitate its passage through the tendinous cords of the mitral valve;

the end of each arm of the bearing member may be made up of several branches, which may move away from each other after passing through the mitral valve cords to form several bearing points under the mitral annulus;

each arm of the bearing member internally comprises an extractable clip to pass through the mitral valve and attach the reinforcement ring;

the free end of each arm of the bearing member comprises a piece of felt or Teflon fabric intended to be laid under the mitral valve and fixed by the clips on the counter-bearing of the reinforcement ring.

BRIEF DESCRIPTION OF THE SEVERAL VIEWS OF THE DRAWINGS

Further characteristics and advantages of the invention will become apparent from the description provided below, which is for reference only and is in no way restrictive, with reference to the accompanying figures, wherein.

DESCRIPTION OF SPECIFIC EMBODIMENTS OF THE INVENTION

Figure 1:
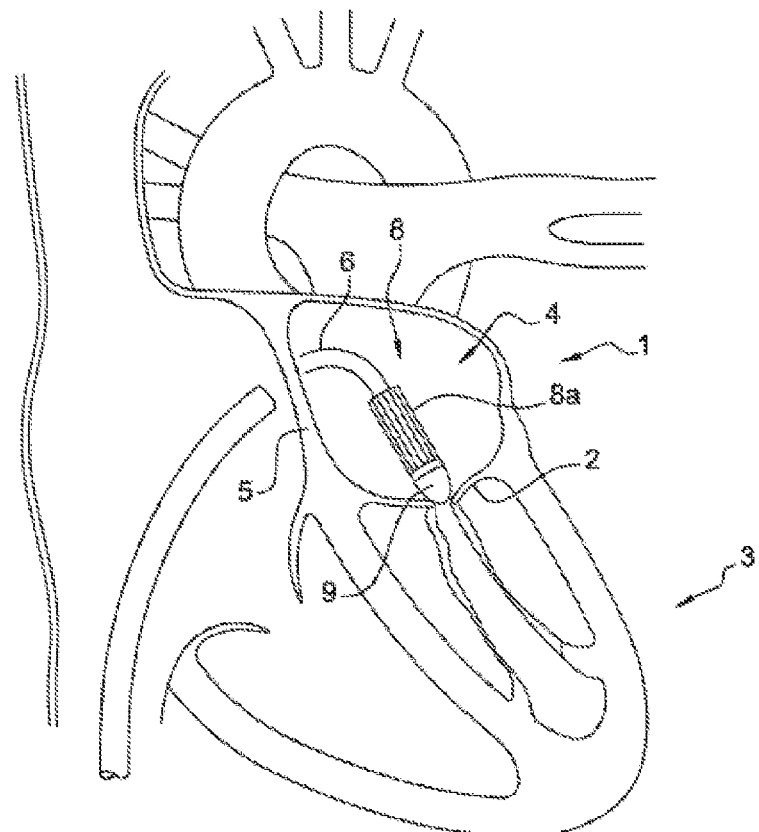
FIG. 1 shows a heart and the insertion, in the left atrium of the heart, of a bearing member of the device in a first embodiment of the invention.
Figure 2:
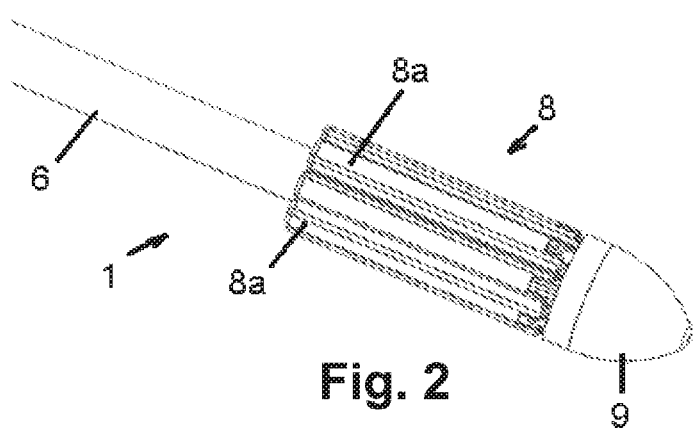
FIG. 2 shows the detail of the bearing member of FIG. 1, in the folded position.

The device (1) of the invention makes it possible to perform a surgical procedure, known as mitral annuloplasty, which consists of repairing the mitral annulus (2) of the heart (3) in a patient suffering from a mitral leak. The device also makes it possible to prepare for a subsequent annuloplasty operation by enabling the placement of a reinforcement ring in the form of a preventive ring, known as a preparation or attachment ring, intended to receive a mitral valve implant at a later time.

The device (1) of the invention is intended to be positioned in a sealed introducer of any known and appropriate type (not shown) and of a diameter less than or equal to 8 mm, placed in a femoral vein to ascend and penetrate the left atrium (4) of the heart (3) through its septal wall (5).

The device (1) comprises a manipulation rod (6), at the end of which an assembly is arranged for the placement and attachment of a reinforcement ring (7), made of fabric for example, at the mitral valve. The other end of the rod (6) is intended to cooperate with a handle under the control of a control means, not shown, for example in the form of a trigger, to operate the assembly.

The device (1) of the invention allows, under radiographic control and after ascending through the vena cava, the entire assembly to penetrate into the left atrium (4) of the heart (3) by passing through the septal wall (5). Next, once the assembly is in the left atrium (4) of the heart (3), it is able to pass through the mitral valve to deploy on the ventricular side below said mitral valve and provide support under the mitral annulus (2).

Two embodiments were realized using this concept, namely a first embodiment illustrated in FIGS. 1 to 12 in which the reinforcement ring (7) is attached from below the mitral valve, and a second embodiment illustrated in FIGS. 13 to 24 in which the reinforcement ring (7) is attached from above the mitral valve.

With reference to FIGS. 1 to 4 and 13 to 16, in both embodiments, the assembly includes a bearing member (8) having a plurality of arms (8a) connected pivotably to a cylinder (9) arranged at the end of the rod (6). The rounded end of the cylinder (9) is atraumatic. The arms (8a) are articulated and mounted pivotably to move, under the action of the control means, from a folded position (FIG. 2 or FIG. 14) along the rod (6) to a deployed position (FIG. 4 or FIG. 16), in the manner of an umbrella, away from the rod (6).

Figure 3:
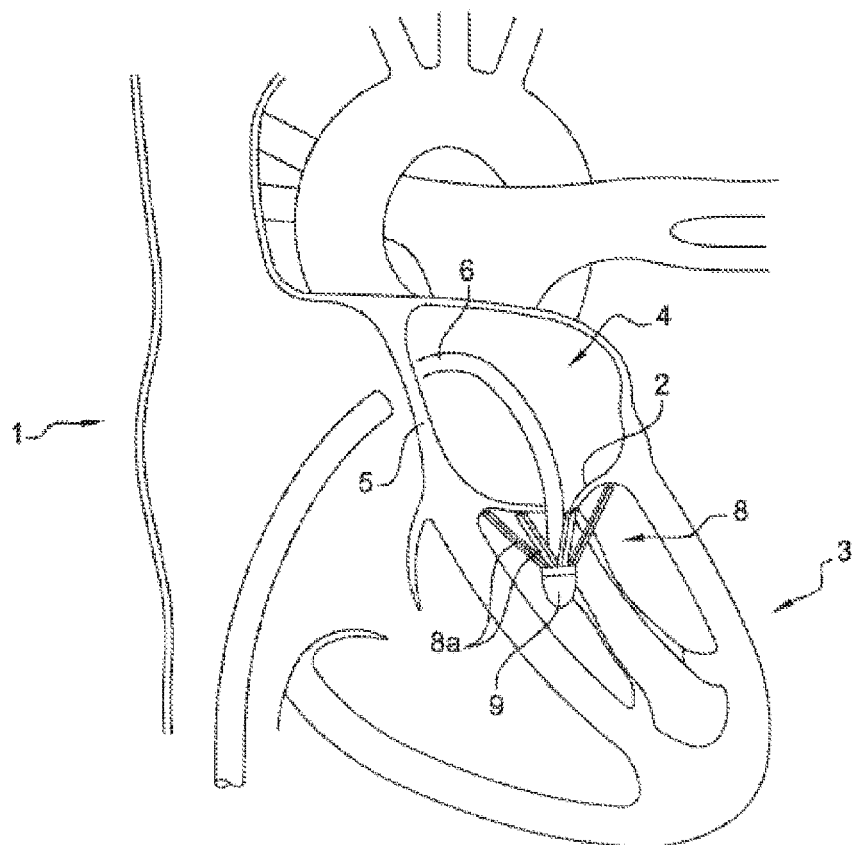
FIG. 3 shows the heart and deployment of the bearing member and its support position under the mitral valve.
Figure 4:
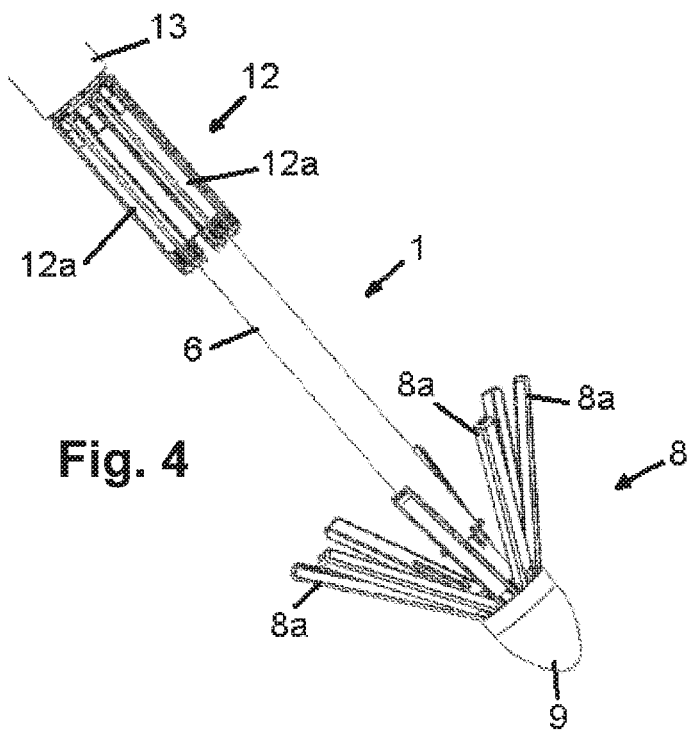
FIG. 4 shows the detail of the bearing member in the deployed position.
Figure 5:
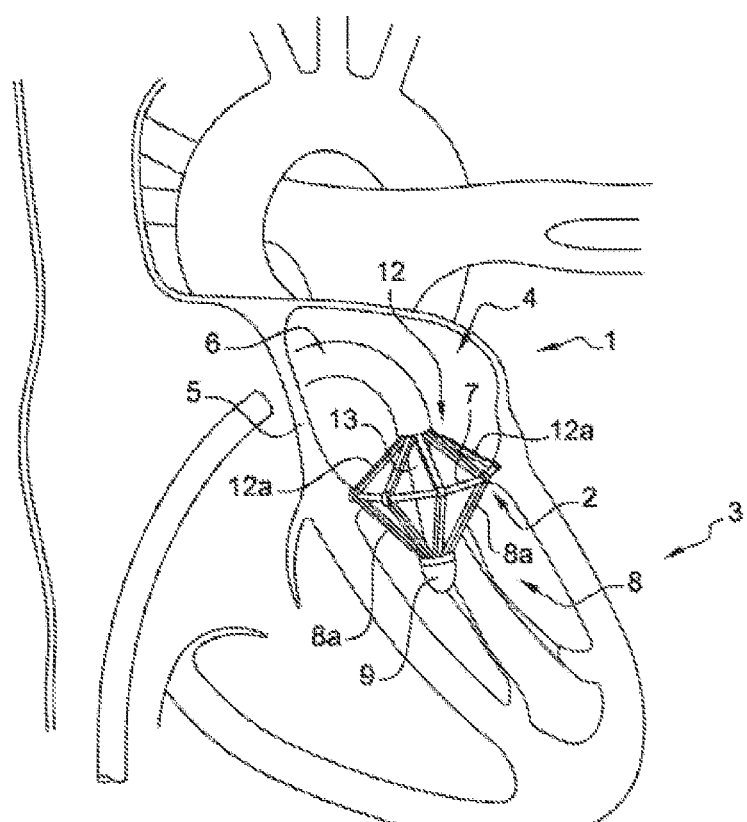
FIG. 5 shows the heart and the deployment of a counter-bearing member per the device, for positioning a reinforcement ring on the mitral valve to counter-support the bearing member.
Figures 6, 7:
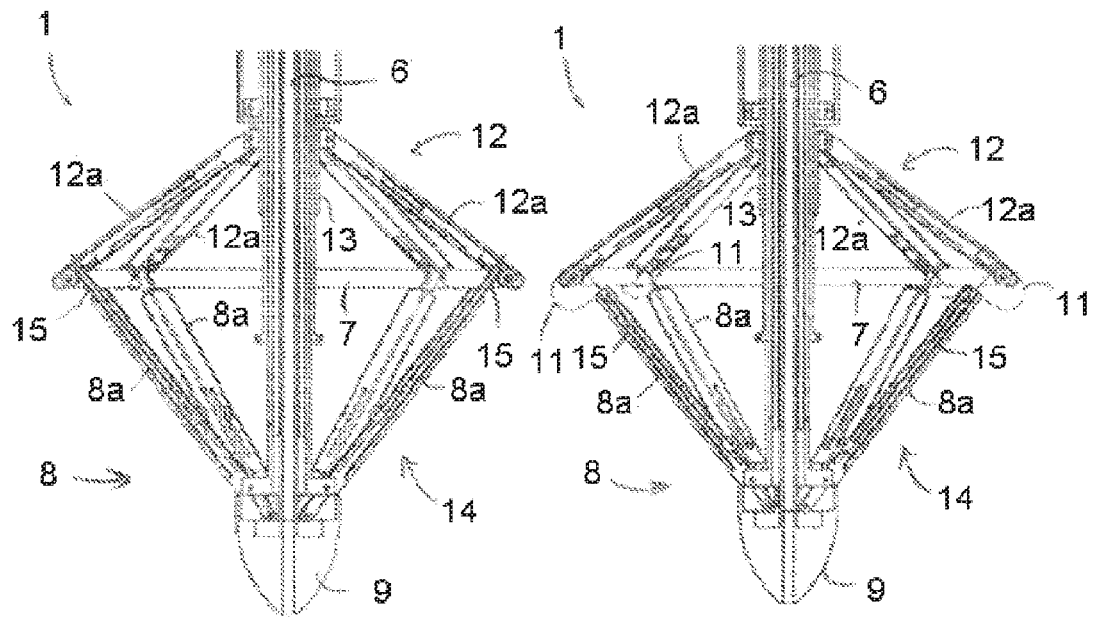
FIG. 6 shows the extraction of the needles arranged inside the arms of the bearing members, allowing sutures for attaching the reinforcement ring to be released.
FIGS. 7 and 7A show the release of sutures through the needles in FIG. 6.
Figures 8, 9:
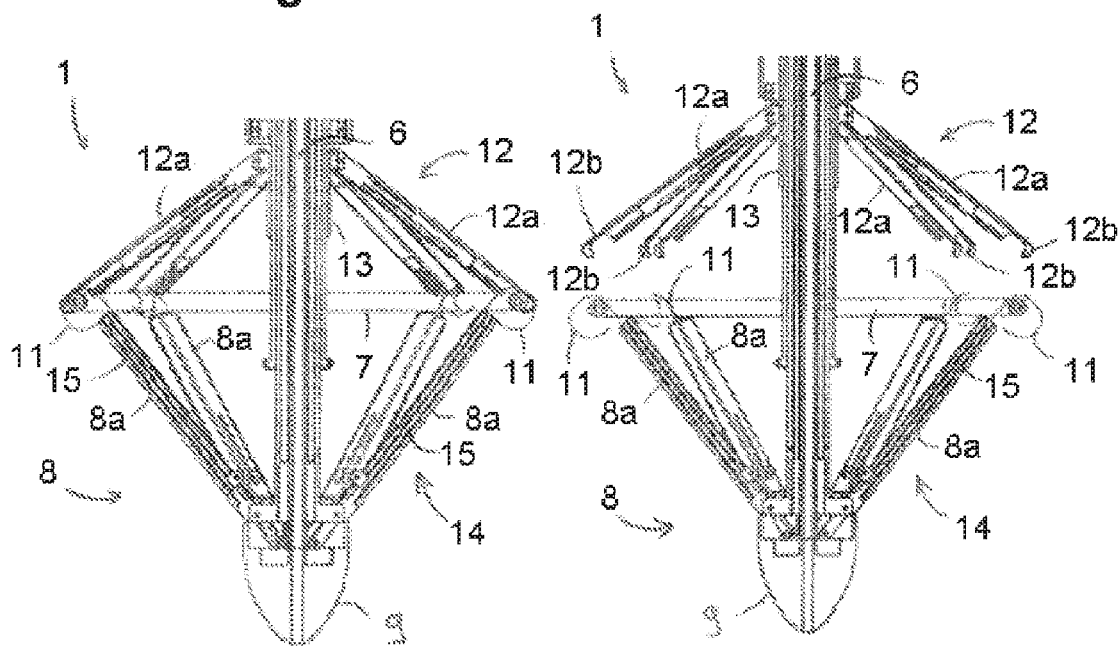
FIGS. 8 and 8A show the disengagement between the arms of the counter-bearing member and the reinforcement ring, in particular by sliding of a carriage.
FIG. 9 shows the removal of the counter-bearing member.
Figures 15, 16:
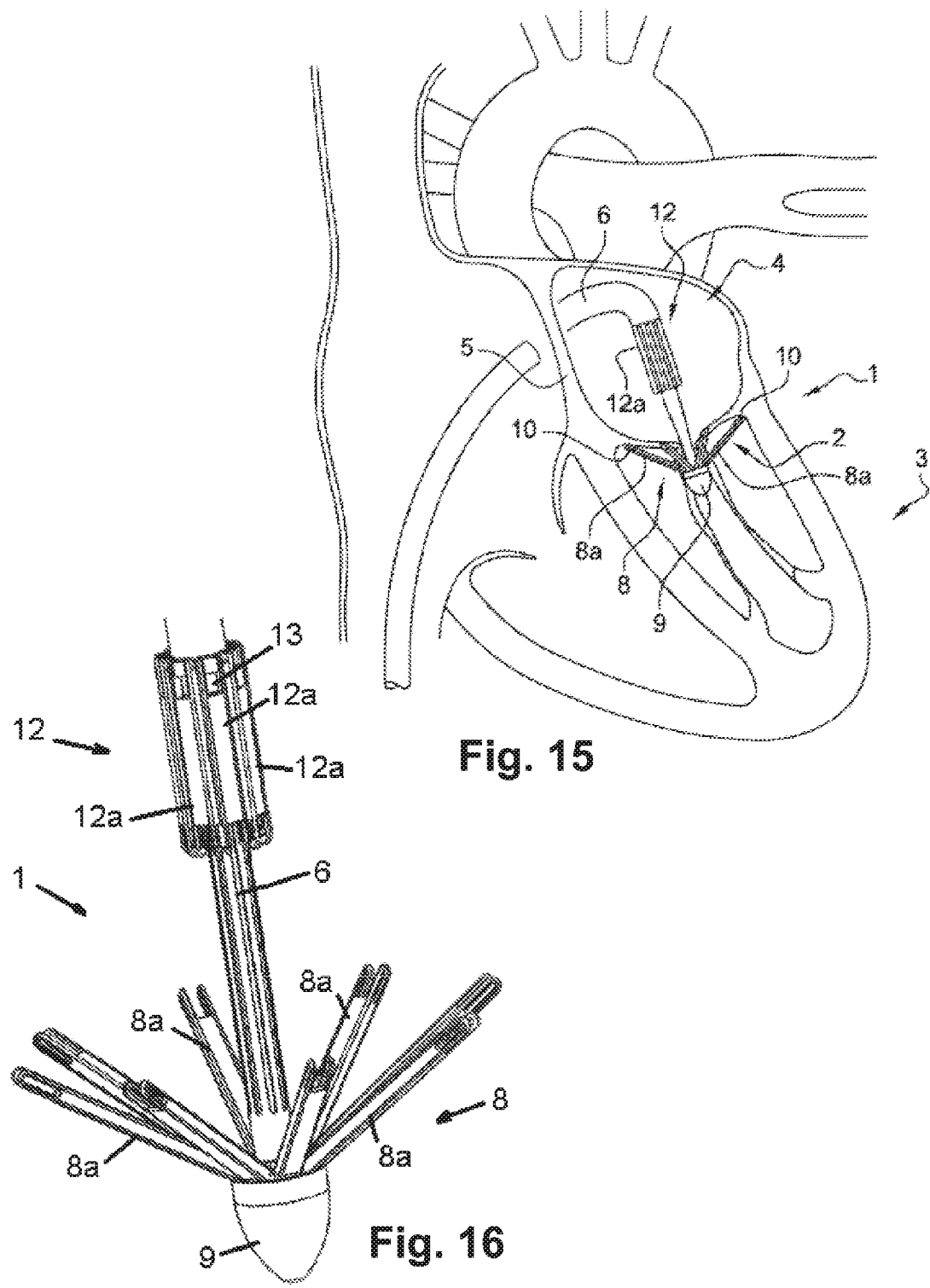
FIG. 15 shows the heart and deployment of the bearing member and its support position under the mitral valve, with pieces of felt or Teflon fabric arranged at the end of the arms of the bearing member and laid under the mitral annulus.
FIG. 16 shows the detail of the bearing member in the deployed position.
Figure 17:
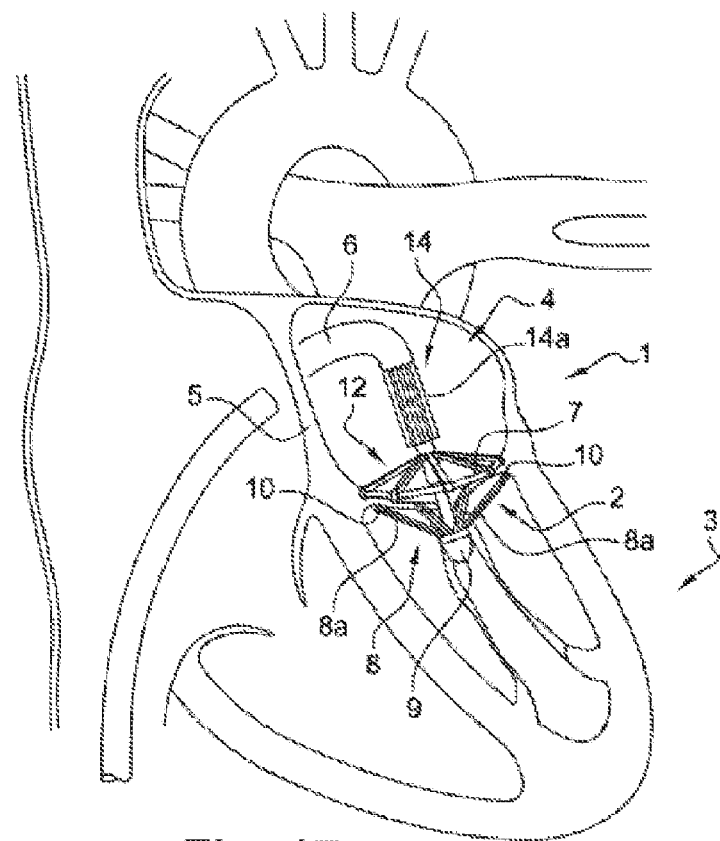
FIG. 17 shows the heart and the deployment of a counter-bearing member per the device, for positioning a reinforcement ring on the mitral annulus to counter-support the bearing member.
Figure 18:
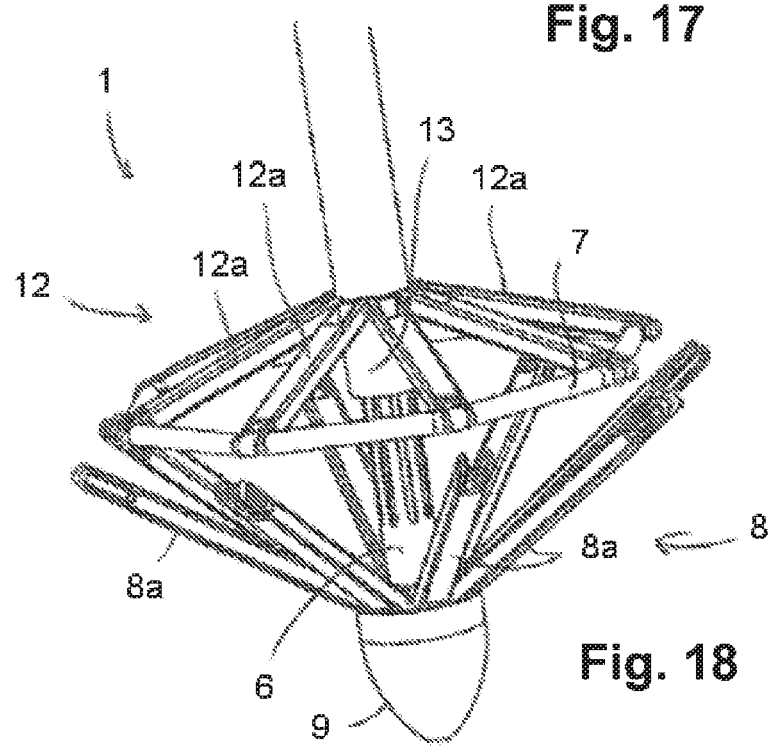
FIG. 18 shows the detail of the counter-bearing member in deployed positions.
Figure 19:
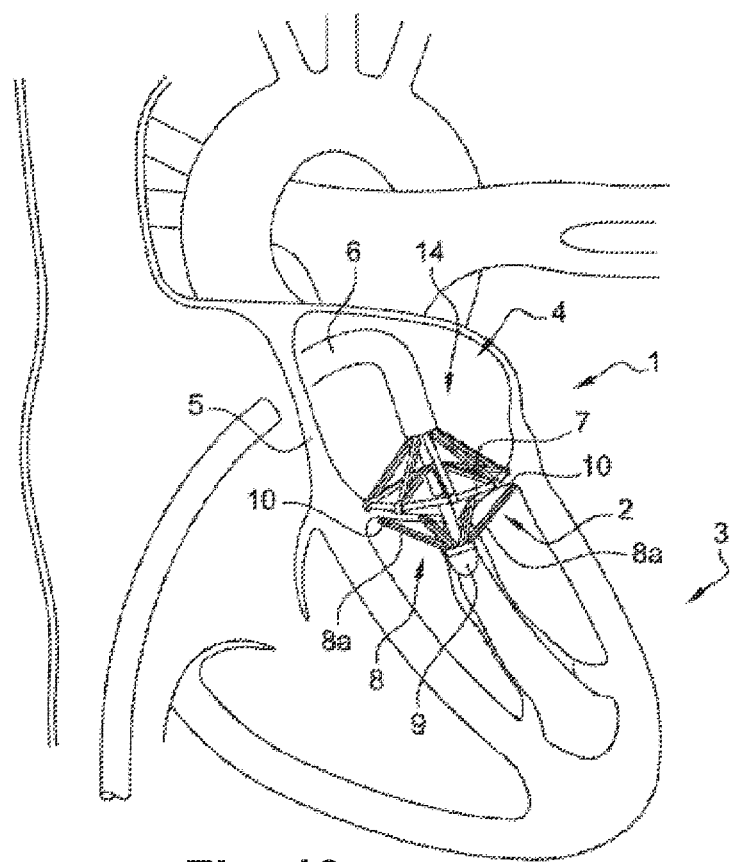
FIG. 19 shows the heart and deployment of the arms that comprise the suture extraction means, aligned with the arms of the counter-bearing member.

Then, by pulling on the rod (6) and the bearing member (8), the arms (8a) naturally find their way through the mitral valve cords to position themselves just below the mitral annulus (2), in the angle formed by the leaflets and the heart wall, to provide support uniformly distributed along the periphery of the mitral valve, and exert pressure there, see FIG. 3 or FIG. 15. To facilitate the passage of the arms (8a) of the bearing member (8) through the mitral valve cords, each arm can extend in a curved direction or be flexible to adopt a curved position. The length of each arm (8a) can be broken at an articulation point allowing the arm (8a) to be bent around said articulation point. In another embodiment, not shown, the end of each arm (8a) may be composed of several branches, which can move away from each other after passing through the mitral valve cords to form several bearing points under the mitral annulus.

In the second embodiment of the invention, each of the free ends of the arms (8a) of the bearing member (8) is shaped, in the form of a loop for example, to receive a piece of fabric (10) made of felt or Teflon, known to a person skilled in the art as a "pledget". The fabric pieces (10) are intended to be laid under the mitral annulus (2) and fixed by sutures (11) to counter-bear against the reinforcement ring (7), as described below.

In both embodiments, the arms (8a) of the bearing member (8) are deployed manually, either together or selectively and independently of each other, to facilitate passage through the mitral cords and adapt to the geometry of the mitral annulus (2). To adapt more closely to the geometry of the mitral annulus (2), which is not necessarily circular, the arms (8a) are telescopic to offer varying lengths.

In a first variant, the arms (8a) can be deployed by mechanical means (not shown) that are included in the control means. For example, a control knob can be screwed in to extend the arms (8a). In another variant, the arms (8a) are self-expanding and inserted into a sheath (not shown) when in the folded position, and extracted from the sheath in the deployed position. The atraumatic cylinder (9) can be used as a sheath. In this latter configuration, the arms (8a) are connected in a hinged manner to a support, such as a sheath, mounted in a sliding manner on the rod (6) to be housed in the cylinder (9) with the arms (8a) in the folded position.

Figure 7A:
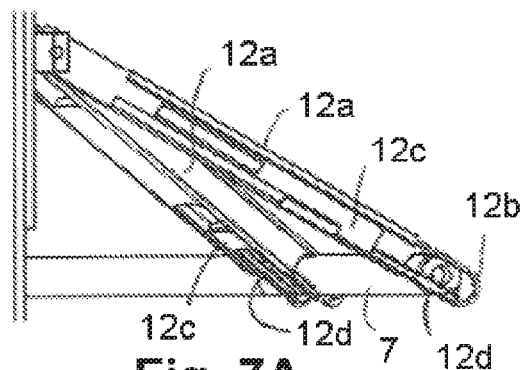
Figure 8A:
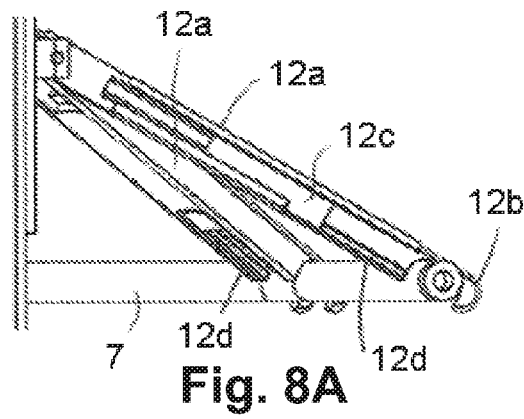
Figure 10:
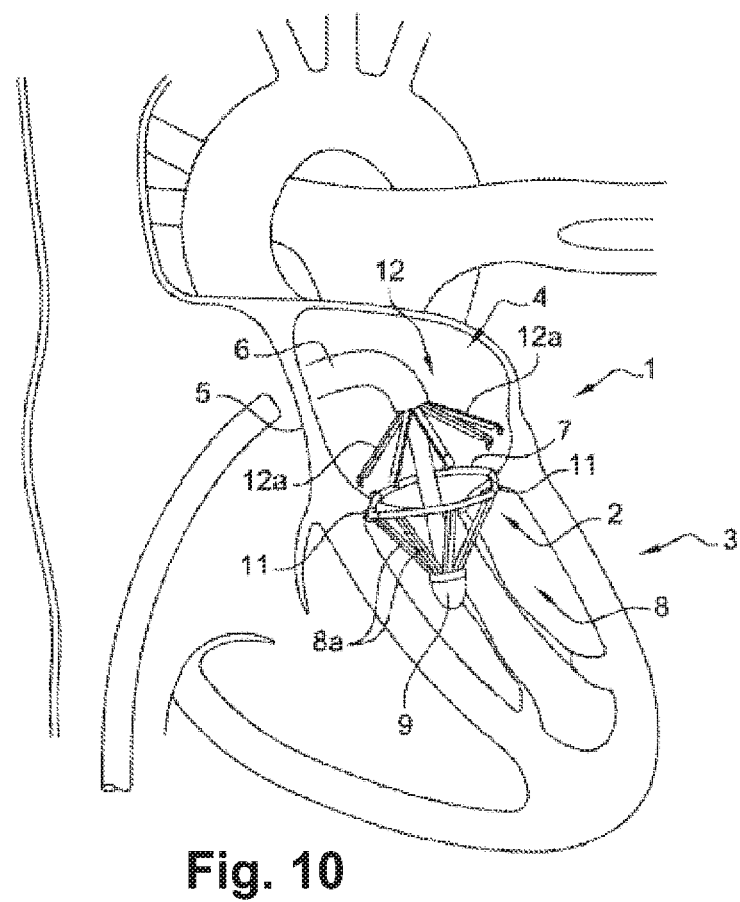
FIG. 10 shows the heart and removal of the counter-bearing member as in FIG. 9.
Figure 11:
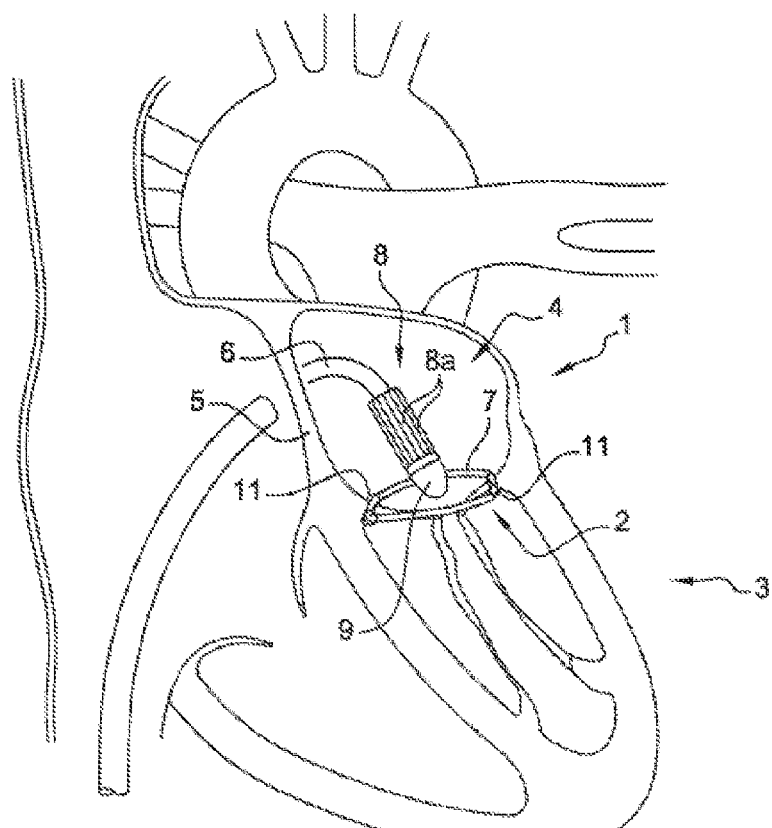
FIG. 11 shows the heart and removal of the bearing member.

With reference to FIGS. 5 to 10 and 17 to 21, the assembly includes a counter-bearing member (12) having a plurality of arms (12a), at the free end of which the reinforcement ring (7) is held. More precisely, each arm (12a) has a free end forming a fork (12b), see FIG. 9, the ends of which are shaped as hooks to hold the reinforcement ring (7). With reference to FIGS. 7A and 8A, each arm (12a) has an inner slide (12c) extended by a spatula blade (12d). The slide (12c) is secured by means (not shown), such as a cable for example, to slide the slide (12c) inside the arm (12a) so that the spatula blade (12d) changes from a locking position for the reinforcement ring (7) in which it is located under the latter (FIG. 7A), to a withdrawn release position for the reinforcement ring (7) (FIG. 8A). The spatula blade (12d) is in the form of two parallel fingers that define a passage for a needle between them as described below.

The arms (12a) of the counter-bearing member (12) are connected pivotably to a support (13), such as a cartridge, arranged coaxially to the rod (6) and mounted along it in a sliding manner. The arms (12a) of the counter-bearing member (12) are articulated and mounted to pivot so that, under the action of the control means, they change from a folded position along the rod (6) to a deployed position away from the rod (6) to create the counter-support on the mitral annulus (2) and position the reinforcement ring (7) under counter-pressure against the arms (8a) of the bearing member (8). As with the arms (8a) of the bearing member (8), the arms (12a) of the counter-bearing member (12) can be deployed simultaneously or selectively and independently of each other, and be telescopic, self-expanding, and arranged in a sheath in the folded position.

From the above, the arms (8a) of the bearing member (8) and the arms (12a) of the counter-bearing member (12) open like an umbrella and align on either side of the mitral annulus (2) to form a bearing/counter-bearing arrangement. This characteristic then makes it possible to pierce through the mitral annulus (2) in a simple, ideal, and traction-free manner to attach the reinforcement ring (7), as described below, by means (14) of suture extraction (11).

As mentioned above, the two embodiments presented differ in the technique of how the reinforcement ring is attached (7).

In the first embodiment, and with reference to FIGS. 6 to 9, the reinforcement ring (7) is attached from below the mitral valve and the sutures (11) are extracted from the arms (8a) of the bearing member (8), which thus form the means (14) for extracting sutures (11). Thus each arm (8a) comprises an internally mounted needle (15) with the translation displacement ability to extend beyond the free end of the arms (8a), and release the sutures (11) to attach the reinforcement ring (7). The needles (15) are shaped to allow the sutures (11) extending from the needle (15) to be engaged, guided, and held in place.

In a first example of implementation, the needles (15) are intended to be extracted to pierce the mitral annulus (2) and protrude from the upper side of the mitral annulus (2), opening into the inside of the fingers (12d) and forks (12b) of the corresponding arms (12a) of the counter bearing member (12). Next, each suture (11) in the form of a thread (11a) made of shape-memory material will automatically, after being released from the needle (15), be twisted to create an anchor loop around the reinforcement ring (7) and in the thickness of the mitral annulus (2) to allow said reinforcement ring (7) to be attached to the mitral annulus (2).

Figure 25:
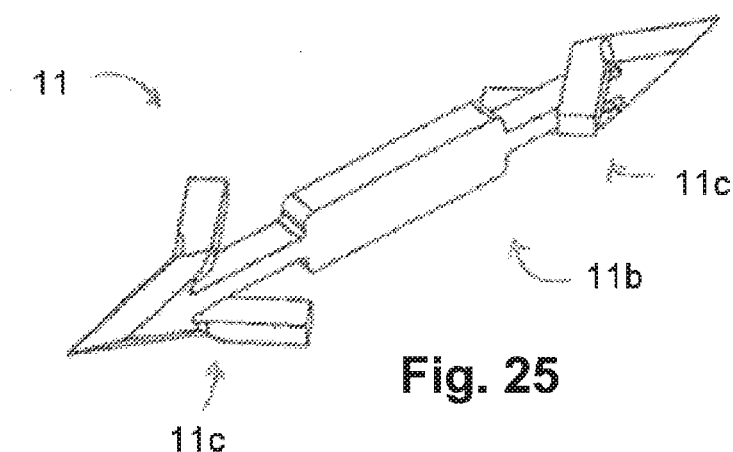
FIGS. 25, 26 and 27 show, in perspective, possible alternate embodiments of the attachment sutures for the reinforcement ring.
Figure 26:
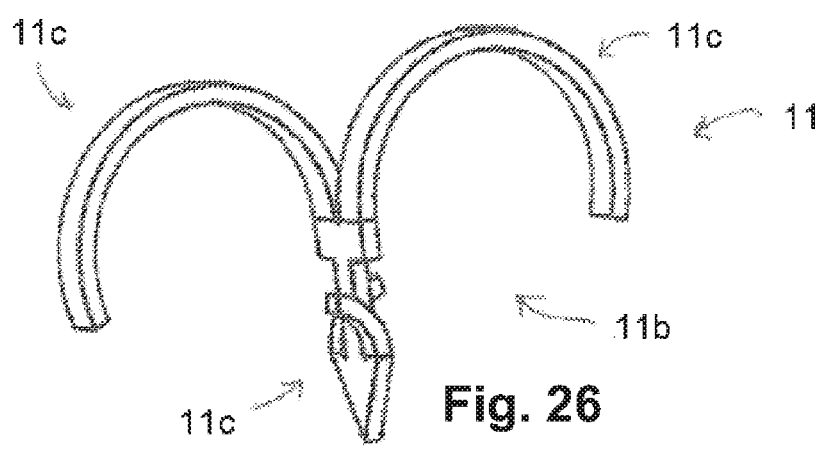
Figure 27:
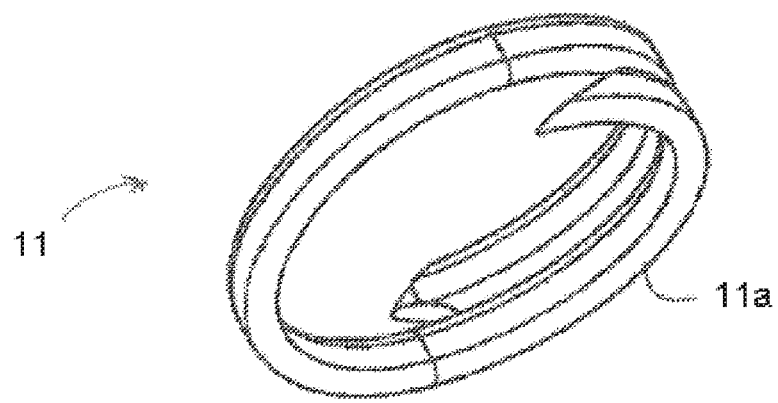

In a second example of implementation, the needles (15) do not pierce the mitral annulus (2) and deliver sutures (11) in the form of clips (11b) that are shaped into a point to pass through the mitral annulus (2) and the reinforcement ring (7) on their own, and which include anchoring portions (11c), such as harpoon-shaped ends, to prevent removal of said clips (11b) and to secure the attachment of the reinforcement ring (7) to the mitral annulus (2). Examples of the embodiments of the different clips (11b) and thread (11a) are shown in FIGS. 25 to 27.

In the second embodiment, and with reference to FIGS. 17 to 21, the reinforcement ring (7) is attached from above the mitral annulus (2). Thus, in this embodiment the means (11) for suture extraction (14) comprise a plurality of arms (14a) pivotally connected to a bearing (15), such as a cartridge, arranged coaxially to the rod (6) such that, under the action of the control means, they change from a folded position along the rod (6) to a deployed position away from the rod (6).

When the arms (14a) of the extraction means (14) are in the deployed position, they align with the arms (12a) of the counter-bearing member (12). For the reinforcement ring (7) to be attached, each arm (14a) comprises internally and in the same way as for the first embodiment, a needle (15) to deliver a suture in the form of a thread (11a) or a clip (11b) intended to be anchored on the periphery of the mitral valve and to attach the reinforcement ring (7) there. The operation is identical and is not described again. In this embodiment, the sutures (11) attach the fabric parts (10) as reinforcement and counter-support to the reinforcement ring (7) on the other side of the mitral annulus (2). The fabric pieces (10) form reinforcements for the sutures (11), so that the tension of the suture (11) is distributed over the entire fabric piece (10) and not directly on the mitral annulus (2). The fabric pieces (10) provide protection against trauma due to the tension of the suture (11).

As with the arms (8a) of the bearing member (8) or the arms (12a) of the counter-bearing member (12), the arms (14a) of the extraction means (14) can be deployed simultaneously or selectively and independently of each other, and be telescopic, self-expanding, and arranged in a sheath in the folded position.

Figure 20:
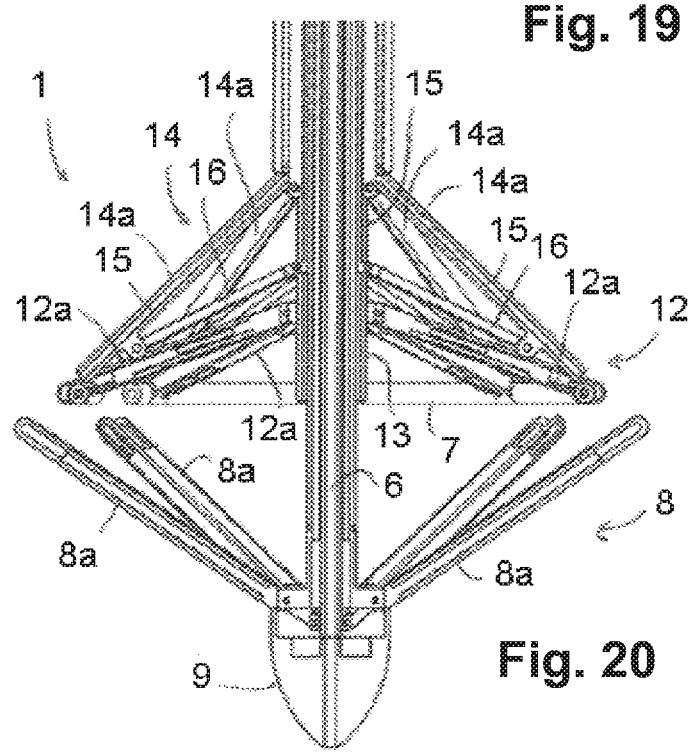
FIG. 20 shows the detail of the deployment of the extraction means arms as shown in FIG. 19.
Figure 21:
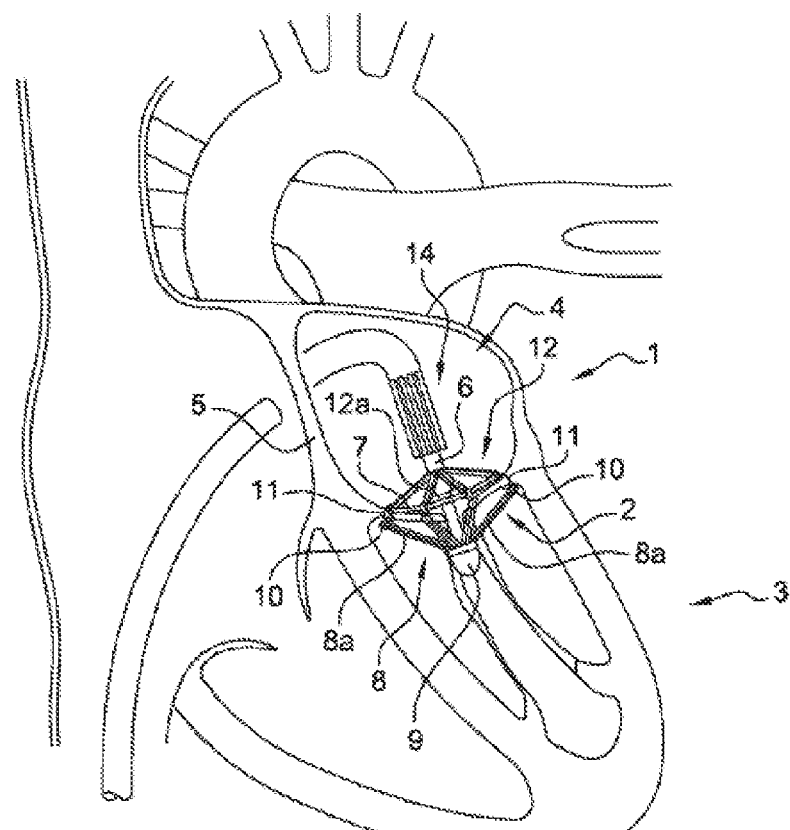
FIG. 21 shows the removal of the suture extraction means, after releasing said sutures and attaching the reinforcement ring to the mitral annulus.
Figure 22:
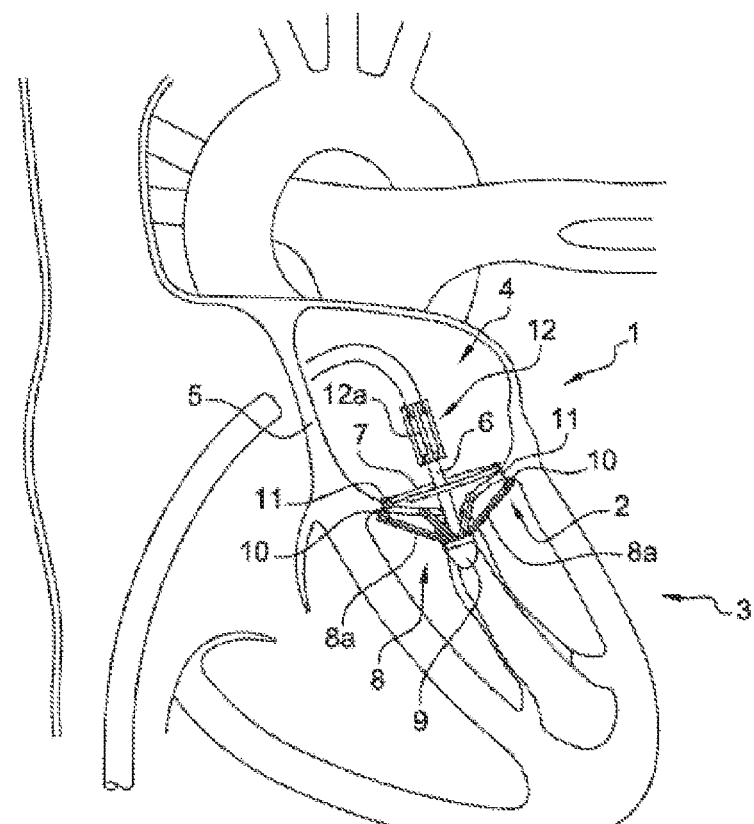
FIG. 22 shows the removal of the counter-bearing member.
Figure 23:
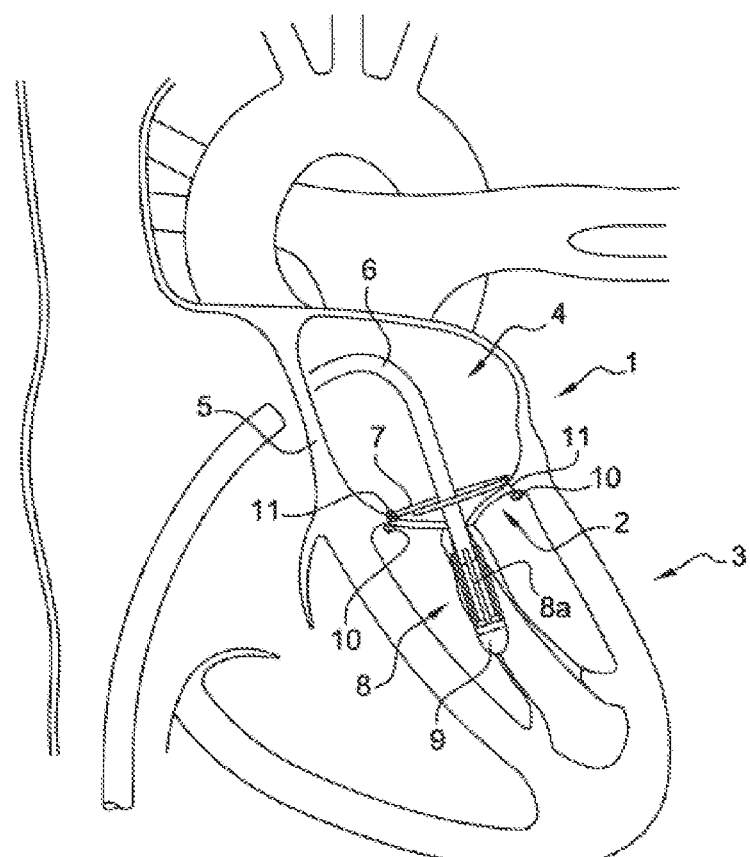
FIG. 23 shows the removal of the bearing member.

With reference to FIG. 20, the free end of each arm (14a) included in the extraction means (14) is connected to the bearing element (15) by a linking rod (16) to form a stable support during the procedure to suture and attach the reinforcement ring (7).

Figure 12:
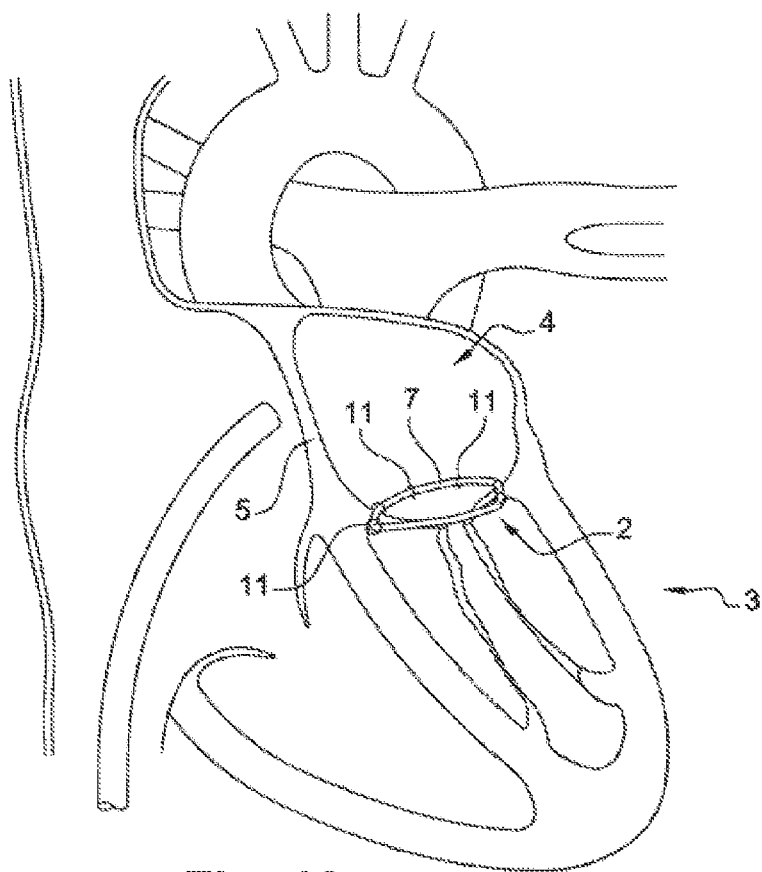
FIG. 12 shows the heart with the reinforcement ring attached to the mitral annulus.
Figure 13:
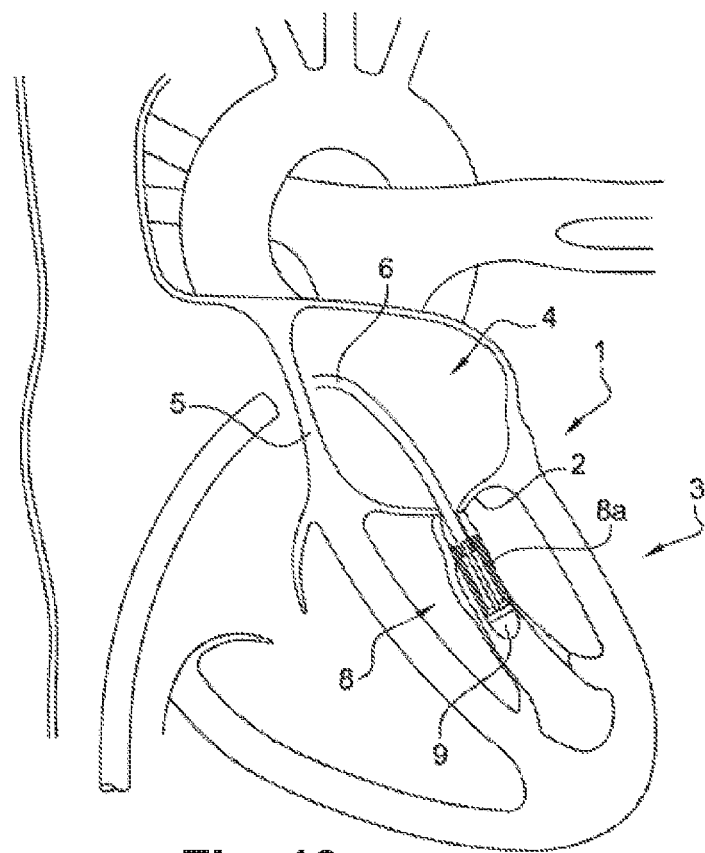
FIG. 13 shows a heart and the insertion, in the left atrium of the heart, of a bearing member of the device in a second embodiment of the invention
Figure 14:
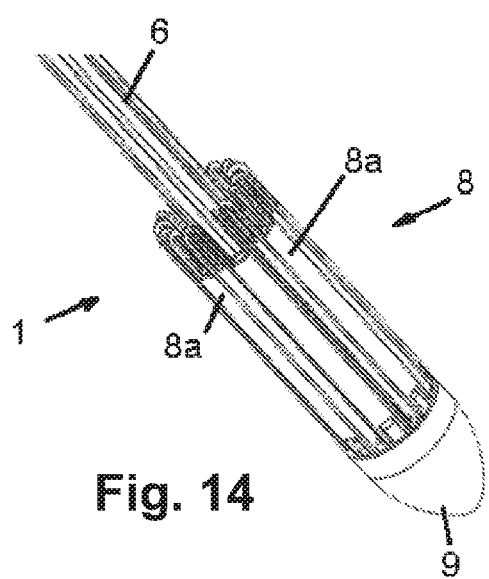
FIG. 14 shows the detail of the bearing member of FIG. 13, in the folded position.
Figure 24:
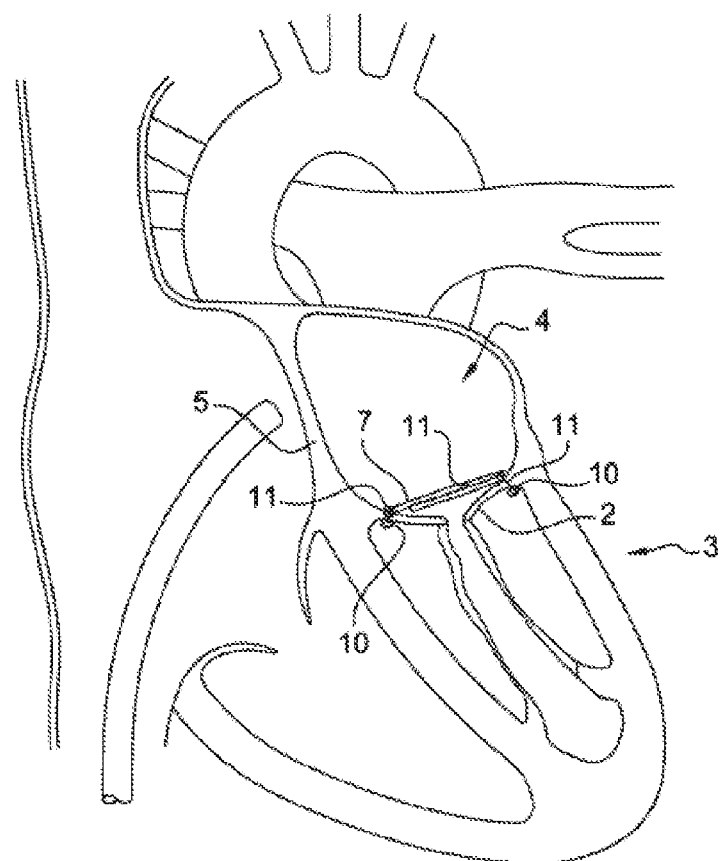
FIG. 24 shows the heart with the reinforcement ring attached to the mitral annulus as counter-support with the fabric parts laid on the other side of the mitral valve to protect it.

With reference to FIGS. 10 to 12 and 21 to 24, when the reinforcement ring (7) is finally attached, and the spatula blades (12d) have been retracted to release the reinforcement ring (7), the various elements of the assembly have each in turn gone into their folded position and are extracted from the heart one by one (3). FIGS. 12 and 24 show the reinforcement ring (7) attached to the mitral annulus (2).

The reinforcement ring (7) is a prosthetic implant capable of decreasing the caliber of the mitral annulus (2) to reduce or even eliminate mitral leaks. In another important characteristic, the reinforcement ring (7) is secured to a means (not shown) capable of reducing its circumference after it is placed and attached to the periphery of the mitral annulus (2), as indicated. For example, these means consist of a traction cord mounted freely in translation and freely sliding in the central core of the reinforcement ring (7) to enable, under traction, the ring to be crimped and, consequently, its diameter reduced. These provisions are particularly important to ensure that after the reinforcement ring (7) has been attached under the indicated conditions, the diameter of the implant can be perfectly adapted, ensuring that there are no further leaks.

To this end, the surgeon removes the device (1), and only the two ends of the thread (11a) that constitute the axial core of the ring protrude from the introducer. Under radiographic control, the exertion of simple traction on the thread simultaneously tightens the valve ring. After finding the proper tension for the right diameter, the thread can be crimped with a knot or clipped and then cut.

The characteristics of the device (1) of the invention provide many advantages over existing solutions. Using the transfemoral route reduces the duration and invasiveness of the procedure. A two-dimensional ultrasound section of the atrioventricular junction can visualize the desired position of the device (1) on the small mitral valve on the ventricular side. Placement is guided by the anatomy of the tissues themselves and the resistance that the operator perceives in the stop position of the bearing member (8) and the counter-bearing member (12)

It should also be noted that the device (1) allows two opposing bearing and counter-bearing forces to be exerted to perforate the tissues and allow the anchoring sutures (11) to pass through without risk of weakening said tissue by eliminating the risks of trial and error. In other words, the mitral annulus tissue (2) and adjacent tissues are more effectively perforated at a single time with optimal holding of the sutures (11).

Finally, it should be noted that the arms (8a) of the bearing member (8) and/or the arms (12a) of the counter-bearing member (12) and/or the arms (14a) of the extraction means (14) each include a radiopaque and/or ultrasound marker allowing the surgeon to perform 2D or 3D control of their position as the operation progresses.

The invention claimed is:

1. Device (1) for performing or preparing a transfemoral annuloplasty of the mitral valve of a heart (3), and intended to be positioned in a sealed introducer placed in a femoral vein to penetrate the left atrium (4) of the heart (3) through its septal wall (5), comprising an assembly for cooperating with a handle under the control of a control means for actuating the assembly for placing and attaching a reinforcement ring (7) on the mitral annulus (2), with said assembly arranged at the end of a handling rod (6) and comprising:

a bearing member (8) comprising a plurality of arms (8a) connected pivotably to the end of the rod (6) so as to change, under the action of the control means, from a position folded along the rod (6) to a deployed position spaced away from the rod (6) in order to provide support under the mitral annulus (2) in a manner uniformly distributed along the periphery of the mitral valve;

a counter-bearing member (12) comprising a plurality of arms (12a), at the free end of which arms the reinforcement ring (7) is arranged, with the arms (12a) connected pivotably to a support (13) disposed coaxially with respect to the rod (6) in such a way as to change, under the action of the control means, from a position folded along the rod (6) to a deployed position spaced away from the rod (6) in order to realize the counter-support on the mitral annulus and position the reinforcement ring (7);

means (14) for removing sutures (11) to attach the reinforcement ring (7) to the mitral annulus.

2. A device (1) as in claim 1, in which the arms (8a) of the bearing member (8) and/or the arms (12a) of the counter-bearing member (12) are connected pivotably to a support (13) disposed coaxially with respect to the rod (6) in such a way as to change, under the action of the control means, simultaneously or selectively and independently from each other, from the folded position to the deployed position.

3. A device (1) as in claim 1, in which the arms (8a) of the bearing member (8) and/or the arms (12a) of the counter-bearing member (12) are arranged inside a sheath in the folded position, and are pushed out of the sheath and are self-expanding in the deployed position.

4. A device (1) as in claim 1, in which the arms (8a) of the bearing member (8) and/or the arms (12a) of the counter-bearing member (12) each include a radiopaque and/or ultrasound marker.

5. A device (1) as in claim 1, in which the arms (8a) of the bearing member (8) and/or the arms (12a) of the counter-bearing member (12) are telescopic.

6. A device (1) as in claim 1, in which the means (14) to allow the extraction of sutures (11) comprise a plurality of arms (14a) connected pivotably to a support (15) disposed coaxially to the rod (6) so as to change, under the action of the control means, from a folded position along the rod (6) to a deployed position spaced away from the rod (6) that aligns with the arms (12a) of the counter-bearing member (12), each arm (14a) internally comprising an extractable suture (11) to anchor on the periphery of the mitral valve and to fix the reinforcement ring thereto (7).

7. A device (1) as in claim 1, in which each arm (8a) of the bearing member (8) is curved, articulated, or flexible to facilitate its passage through the tendinous cords of the mitral valve.

8. A device (1) as in claim 1, in which the end of each arm (8a) may be composed of several branches, which can move away from each other after passing through the mitral valve cords to form several support points under the mitral annulus.

9. A device (1) as in claim 1, in which each arm (8a) of the bearing member (8) internally comprises an extractable suture (11) to go through the mitral annulus (2) and attach the reinforcement ring (7).

10. A device (1) as in claim 6, in which the free end of each arm (8a) of the bearing member (8) comprises a piece of felt or Teflon fabric (10) intended to be laid under the mitral valve (2) and fixed by the sutures (11) to support and counter-bear against the reinforcement ring (7).

* * * * *